(12) United States Patent
Benz et al.

(10) Patent No.: US 9,427,239 B2
(45) Date of Patent: Aug. 30, 2016

(54) APPARATUS AND METHOD OF USE FOR AN ADJUSTABLE RADIAL AND ULNAR COMPRESSION WRISTBAND

(71) Applicant: Semler Technologies, Inc., Milwaukie, OR (US)

(72) Inventors: Philip Benz, Portland, OR (US); Matthew Semler, Portland, OR (US)

(73) Assignee: Semler Technologies, Inc., Milwaukie, OR (US)

(*) Notice: Subject to any disclaimer, the term of this patent is extended or adjusted under 35 U.S.C. 154(b) by 110 days.

(21) Appl. No.: 14/329,080

(22) Filed: Jul. 11, 2014

(65) Prior Publication Data

US 2015/0018869 A1 Jan. 15, 2015

Related U.S. Application Data

(60) Provisional application No. 61/957,817, filed on Jul. 12, 2013, provisional application No. 61/976,978, filed on Apr. 8, 2014.

(51) Int. Cl.
| | |
|---|---|
| *A61B 17/132* | (2006.01) |
| *A61B 17/135* | (2006.01) |
| *A61B 17/12* | (2006.01) |
| *A61B 5/022* | (2006.01) |

(52) U.S. Cl.
CPC ......... *A61B 17/135* (2013.01); *A61B 17/1325* (2013.01); *A61B 5/02233* (2013.01); *A61B 17/12* (2013.01); *A61B 17/12009* (2013.01); *A61B 17/132* (2013.01); *A61B 17/1322* (2013.01); *A61B 17/1327* (2013.01); *A61B 17/1355* (2013.01); *A61B 2017/12004* (2013.01); *A61B 2090/0807* (2016.02)

(58) Field of Classification Search
CPC ........... A61B 17/12; A61B 17/12009; A61B 17/132; A61B 17/1322; A61B 17/1325; A61B 17/1327; A61B 17/135; A61B 17/1355; A61B 2017/12004; A61B 5/02233
See application file for complete search history.

(56) References Cited

U.S. PATENT DOCUMENTS

| | | | | |
|---|---|---|---|---|
| 5,413,582 | A * | 5/1995 | Eaton | A61B 17/135 600/499 |
| 5,643,315 | A * | 7/1997 | Daneshvar | A61B 17/135 606/201 |
| 2004/0098035 | A1* | 5/2004 | Wada | A61B 17/1325 606/201 |
| 2009/0234261 | A1* | 9/2009 | Singh | A61B 17/1325 601/152 |
| 2010/0179586 | A1* | 7/2010 | Ward | A61B 17/1325 606/202 |
| 2013/0237866 | A1* | 9/2013 | Cohen | A61B 17/1325 600/502 |

OTHER PUBLICATIONS

Samir Pancholy MD, et al. "Prevention of Radial Artery Occlusion-Patent Hemostasis Evaluation Trial (PROPHET Study)" Catheterization and Cardiovascular Interv 72:335-34 (2008).

(Continued)

*Primary Examiner* — Todd J Scherbel

(57) ABSTRACT

An adjustable radial and ulnar vascular compression wristband assists in achieving partial or full occlusion of a blood vessel when applied to a patient's wrist during or following a medical procedure. At least two adjustably inflatable non-adjacent balloons on the wristband apply preferential compression to portions of the circumference of the wrist, including in particular those portions overlying the ulnar and radial arteries.

12 Claims, 7 Drawing Sheets

(56) References Cited

OTHER PUBLICATIONS

Ivo Bernat MD, et al. "Efficacy and Safety of Transient Ulnar Artery Compression to Recanalize Acute Radial Artery Occlusion . . . " Am J Cardiol 2011;107:1698-1701.

"Guideline: Usage Protocol, Radial Artery Hemostasis, RadAR Vascular Compression Device, Jul. 2012" Semler Technologies, Inc.

* cited by examiner

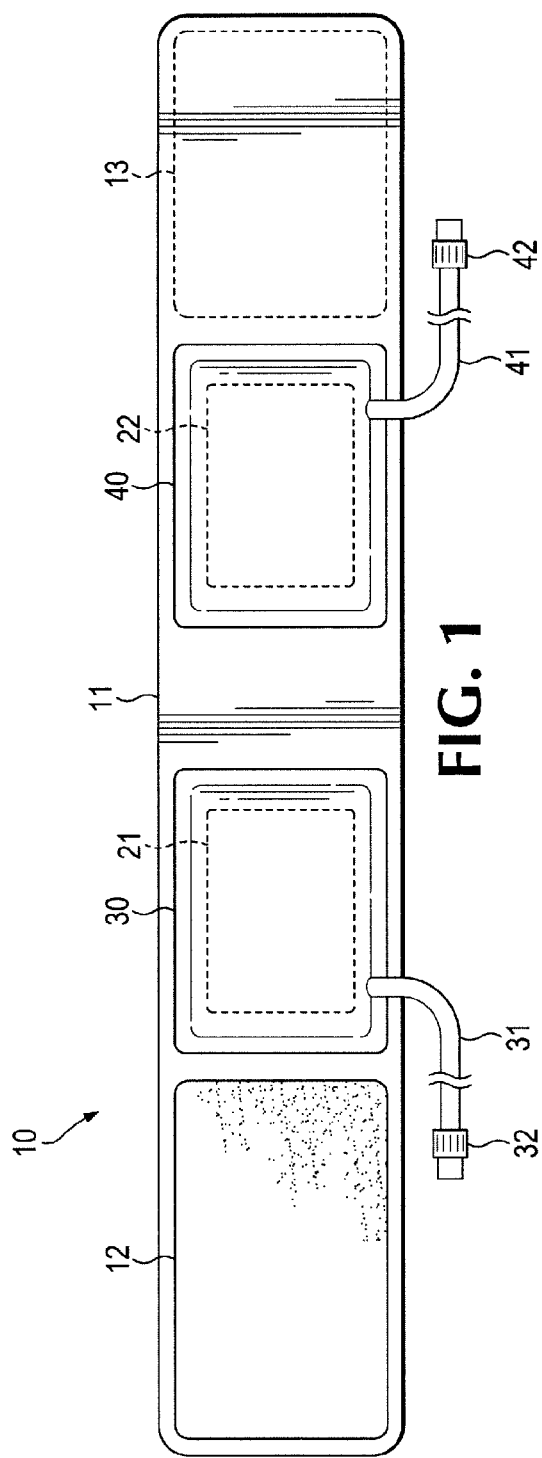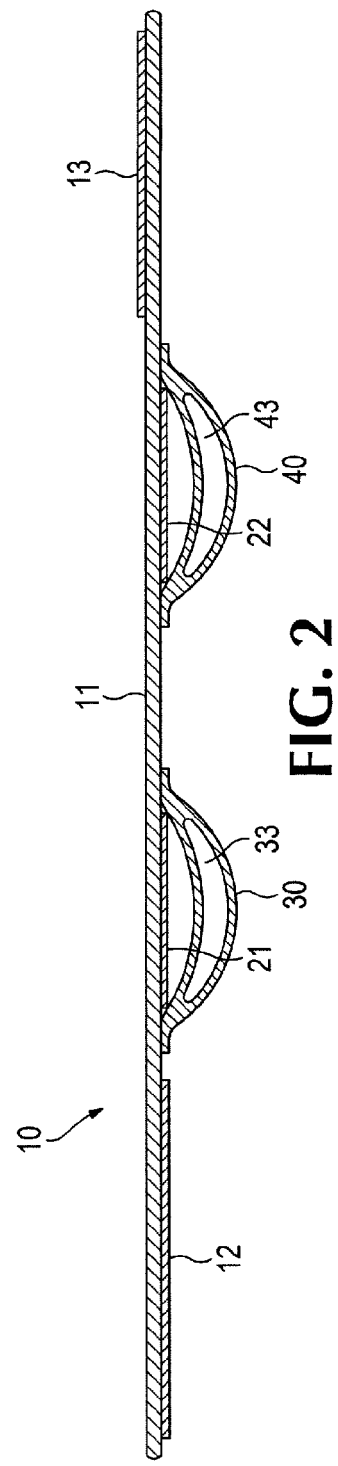

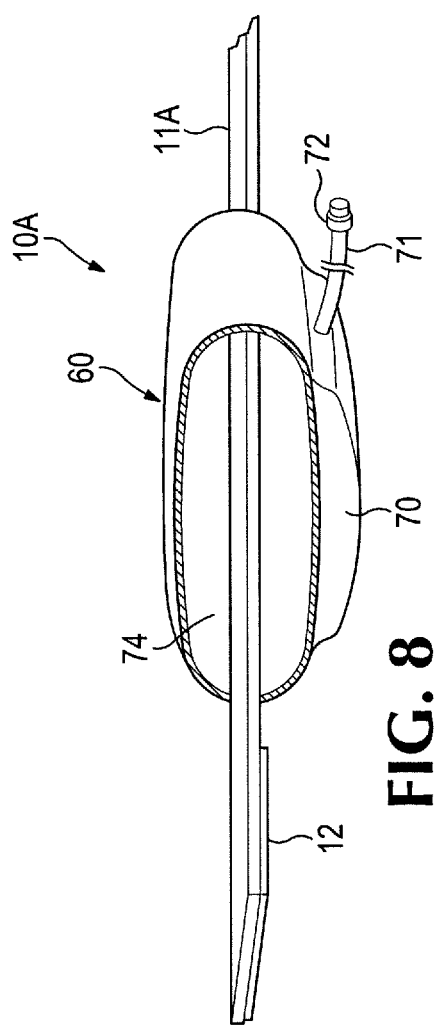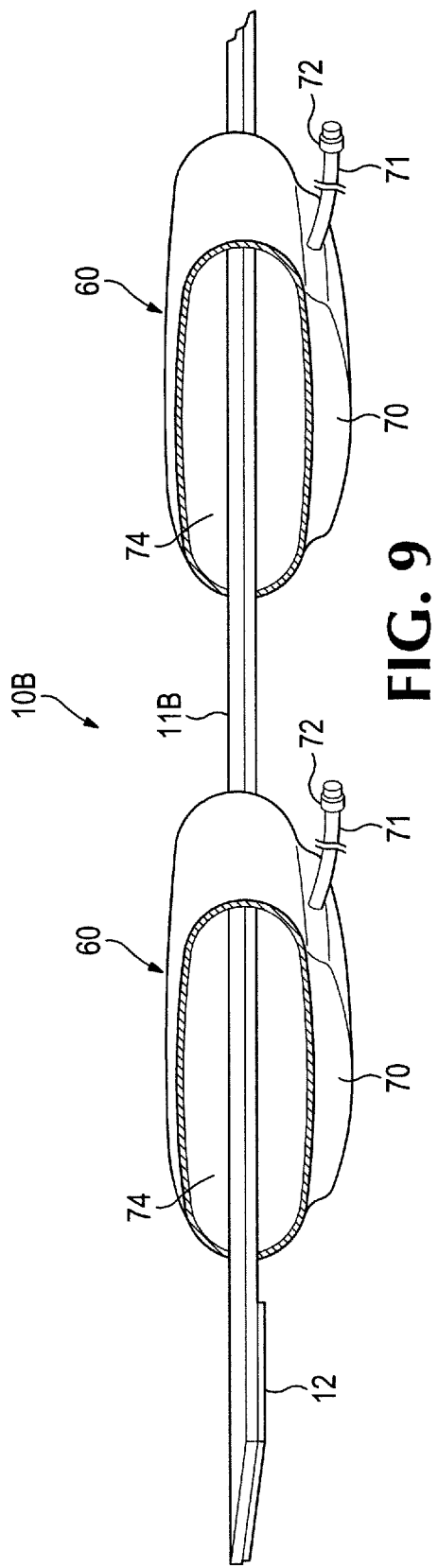

APPARATUS AND METHOD OF USE FOR AN ADJUSTABLE RADIAL AND ULNAR COMPRESSION WRISTBAND

This Non-Provisional Utility Patent Application claims benefit of Provisional Patent Application No. 61/957,817, which has a filing date of Jul. 12, 2013, and Provisional Patent Application No. 61/976,978, which has a filing date of Apr. 8, 2014.

FIELD OF THE INVENTION

The present invention generally relates to compression devices for occluding blood flow through blood vessels in a limb, in particular, the radial and ulnar blood vessels located in a human forearm and wrist. More particularly, the invention relates to a device for reducing or stopping blood flow in said blood vessels by means of adjustably applying compression to the body surface overlying said blood vessels, for the purpose of achieving post-procedure hemostasis at a vascular puncture site used to gain access for catheters or other cannulae to the circulatory system.

BACKGROUND OF THE INVENTION

A number of devices have been utilized to externally compress blood vessels in various parts of the body to reduce or stop the flow of blood through said vessels in order to achieve post-procedure vascular hemostasis. Such devices generally find use in clinical settings, e.g. cardiac catheterization laboratories where minimally invasive procedures are performed on patients, e.g. catheterization of coronary arteries by means of vascular access using catheters inserted through sheaths placed into vascular puncture sites and arteriotomies. Such puncture sites are typically located in an artery close to the patient's skin surface, e.g. a femoral artery in the groin area or radial artery in the wrist area. At the end of these procedures when the catheters and sheath are to be withdrawn, devices that externally compress blood vessels are often used to achieve hemostasis at the puncture site and arteriotomy. Also used is manual compression, i.e. external compression applied by an operator's hands or fingers.

Sometimes used in conjunction with such external compression are hemostatic agents, which assist in achieving hemostasis of a puncture site. Examples of such hemostatic agents are powders, and "patches" or pads in various shapes, generally composed of: i) a chitosan or other polysaccharide such as a β-(1-4)-linked D-glucosamine (deacetylated unit) or N-acetyl-D-glucosamine, ii) thrombin, iii) calcium alginate, or iv) minerals such as kaolin or potassium ferrate. Applied to a puncture site and in contact with an amount of blood, these agents can assist in the formation of a clot to accelerate the time to hemostasis.

Several devices, which are known to the inventor, help achieve hemostasis in blood vessels of the forearm using mechanical and/or pneumatic means of applying compression over a blood vessel, for the purpose of allowing a clot to form, thereby enabling hemostasis and corollary cessation of bleeding. Features noted in this art are: i) the use of clamping or inflatable bladder mechanisms to selectively apply compression to those portions of the body surface overlying a target blood vessel and ii) the incorporation of features to gradually reduce compression and permit direct visual observation of a surface wound or puncture site leading to the target vessel.

The prior art teaches that compression applied externally, i.e. on the body surface and over a target blood vessel, slows the blood flow such that a clot can form so that normal hemostasis may occur. The prior art further teaches the value of: i) visual and physical access to the puncture or wound site on the body surface; ii) preferential and adjustable compression over a target vessel, so that arterial flow to or venous return from an extremity, for example a hand, are important attributes of a device having the purpose of achieving hemostasis following catheterization or other cannulation; iii) quickly releasing compression and removing the device from the patient; iv) enabling distal blood flow through adjacent blood vessels, for example, distal blood flow through the ulnar artery and venous return from the hand, while compression over the target vessel is applied; and, v) enabling distal blood flow through the target blood vessel while compression is applied to it.

The term "patent hemostasis" has been coined and was initially described by Samir Pancholy, MD in the PROPHET Study of 2007, where continued perfusion through the radial artery during the period in which external compression is applied for the purpose of achieving hemostasis at the arteriotomy and puncture site is required in order to reduce the incidence of chronic radial artery occlusion, a not-uncommon complication of radial access. He demonstrated that maintaining patency of the radial artery during the hemostasis period and adjusting compression to permit such patent hemostasis helps to avoid chronic radial artery occlusion.

Recently, medical discoveries (Bernat I, et al, "Efficacy and safety of transient ulnar artery compression to recanalize acute radial artery occlusion after transradial catheterization," American Journal of Cardiology, 2011 June 1;107(11): 1698-701. doi: 10.1016/j.amjcard.2011.01.056. Epub 2011 Mar. 23) regarding thrombosis resulting from accessing the radial artery for catheterization have shown an advantage to applying compression over the ulnar artery immediately post-procedure for patients in whom the radial artery is occluded, while avoiding bleeding from the radial puncture site. Achieving simultaneous compression of the ulnar artery during radial artery hemostasis in this fashion was performed using either a second device or applying manual compression (i.e. with the operator's fingers) over the ulnar artery. It's also expected that ulnar compression concomitant with compression over the radial artery for the purpose of achieving hemostasis will result in easier achievement of patent hemostasis in a substantial proportion of patients. Although many compression devices are available for compression of the radial artery there are none known to the inventor that can also simultaneously provide compression of the ulnar artery.

A pneumatically-adjustable device called the TR Band marketed by Terumo, as described in U.S. Pat. No. 7,498,477 by Wada, utilizes a wrist-encircling strap that applies compression by means of two inflatable bladders, one of which directly underlies the other, both for the purpose of compressing only the radial artery. The TR Band is initially attached to the patient using hook and loop fastening after positioning the bladders over the radial artery puncture site; a syringe is then attached to a tube connected to both bladders and air is injected to expand the bladders, thereby applying compression over the puncture site to achieve hemostasis when the sheath is pulled from the vessel. Air can then be gradually withdrawn from the bladders to usually enable patent hemostasis, i.e. blood flow through the radial artery without any bleeding from the arteriotomy and puncture site. The TR Band has no bladder or other compression means to apply compression over the ulnar artery.

Additional attributes of the TR Band include the feature whereby compression over the radial artery during deployment, caused by inflation of the bladders, automatically reduces during deployment without action by the user, through material stretching or automatic release of some of the volume of air contained in the bladders. Anecdotal evidence suggests that this is an undesirable feature if the deflation is excessive, at least when patients on which it is deployed have been administered anti-coagulation medications and/or are hypertensive, both of which are not-uncommon occurrences in cardiac catheterization patients. Such automatic deflation sometimes has the effect of reducing compression to the point that bleeding occurs at the puncture because insufficient compression is applied to stop said bleeding.

Another pneumatically-adjustable compression device is described by Egnelov in U.S. Pat. No. 6,264,673, which is more commonly known by its trade name of Femostop. Comprising a single rigid beam to which two pneumatically inflatable pressure pads and a belt are attached, it is designed specifically to apply compression to either femoral arteries or femoral veins for the simultaneous bilateral compression of said arteries or veins for the purpose of simultaneously providing hemostasis to each of two bilaterally-located puncture sites, one in each artery or vein. Models are also available for puncture sites on only one side of the patient.

Other devices in common usage include the Rad$_{AR}$ Vascular Compression Device as described by Niemeyer in abandoned U.S. Pat Appl. No. 61/198,956. The Rad$_{AR}$ device also applies adjustable compression, however such compression is modulated by mechanical and not pneumatic means. Another device is described by Niemeyer et al in pending U.S. patent application Ser. No. 14/227,160, where the adjustment means is achieved by a double ratcheting action. Another device is the HemoBand, described in U.S. Pat. No. 5,269,803 by Geary that discloses a strap that encircles the forearm with a pressure pad that applies compression over the vessel to prevent bleeding through the puncture. Other mechanically (as compared with pneumatically) operated devices that include a strap to prevent bleeding through a puncture site include: U.S. Pat. No. 4,182,338 to Stanulis; U.S. Pat. No. 4,005,709 by Laerdal; U.S. Pat. No. 3,954,109 by Patel; and U.S. Pat. No. 3,586,001 by Sanderson. Another device that includes a hemostat is the D-Stat Radial, from Vascular Solutions, Inc. Of these mechanical devices, only the Niemeyer devices enable easy adjustment, and none feature any compression means to provide simultaneous compression over the ulnar artery during radial artery compression.

Therefore, a need exists for an adjustable radial and ulnar compression wristband. Such a device is described in the U.S. Provisional Patent Applications No. 61/957,817 filed on Jul. 12, 2013 and No. 61/976,978 filed on Apr. 8, 2014 by Philip Benz, an inventor on this present non-provisional application.

SUMMARY AND OBJECTS OF THE INVENTION

The present invention generally relates to devices for use following cannulation procedures performed on blood vessels in a limb of a patient, in particular on the radial and ulnar arteries, during or after radial artery catheterization procedures. The '817 and '978 provisional utility patent applications by Benz describe an adjustable vascular compression wristband which applies adjustable compression on a patient's body surface overlying the radial and ulnar arteries thereby constricting, to varying degree, said arteries for the purpose of reducing or stopping blood flow at those points of compression, to permit hemostasis to occur at the target vessel puncture site and arteriotomy. Such compression is applied such that blood flow in the target vessel, i.e. the radial artery, is reduced or stopped at both the puncture site and at the arteriotomy, the compression being applied and adjusted independently for the ulnar artery as well as the radial artery. Thus, the invention of '817 and '978 provides utility in assisting with hemostasis following medical cannulation procedures on the limbs of a patient, in particular in radial artery catheterization procedures for interventional cardiology, diagnostic cardiology, radiology, and other cardiac and vascular procedures when catheters, sheaths or other cannulae are withdrawn from a patient's blood vessels.

The radial and ulnar compression wristband of the '817 and '978 invention has features that permit sufficient adjustable compression to be applied to the target blood vessels in a patient's forearm, specifically the radial and ulnar arteries while, at the discretion of the user deploying the device on a patient, maintaining blood flow through these target vessels. For example, the wristband may be used to simultaneously partially or fully occlude blood flow through radial and ulnar arteries, with compression adjustments to gradually increase blood flow as hemostasis occurs, while simultaneously permitting venous return from the hand. As described in '817 and '978, an inflation means is used to apply such compression, an adjustment means is used to adjust said compression in small increments, and a securement means is used to quickly attach and detach the device from the patient's wrist.

The wristband may be formed of biocompatible materials that may be assembled, packaged and pre-sterilized for single-use applications. Alternatively, the wristband may be provided in partially assembled or non-sterilized form.

In view of the above, an object of the adjustable vascular compression wristband of the present invention is to provide a device that provides external compression onto a body surface, which in turn compresses underlying target blood vessels for the purpose of slowing or stopping blood flow to assist in achieving hemostasis of a puncture or wound.

Another object of the present invention is to enable the device to be rapidly applied and fastened to the patient and, following use, rapidly removed from the patient.

Another object of the present invention is to enable a user operating the device to make fine adjustments in the amount of external compression applied to the target blood vessels following device deployment without releasing the fastening mechanism, the adjustments preferably being made independently for each vessel.

Another object of the present invention is to provide a user with both visual and physical access to the puncture site when the compression device is applied to the patient.

Another more particular object of the present invention is to adjustably provide external compression of target blood vessels, specifically the radial and ulnar arteries in the wrist following a catheterization or other medical cannulation procedure, directly over or near to a puncture site on the body surface, which leads to an arteriotomy, for the purpose of stopping or slowing distal blood flow in order to comfortably achieve hemostasis in the artery used to achieve vascular access.

Another more particular object of the present invention is to provide adjustable external compression of the target blood vessels while permitting patent hemostasis to occur in the radial artery, or alternatively in the event that the ulnar artery is used for vascular access, in the ulnar artery.

The wristband of the present invention achieves these and other objects through its inclusion of elements that generally include at least a flexible strap, a securement means for fastening said strap circumferentially around a wrist or forearm, a compression means for applying preferential compression to the surface of a wrist or forearm, more particularly comprising an inflation means for achieving said compression, and an adjustment means for adjusting said compression.

The strap may therefore include, in the context of the embodiments described in this specification, a flexible strap having two ends, hook and loop material placed at opposite ends of the strap, at least two non-adjacent inflatable balloons to be positioned over the radial and ulnar arteries, connectors and valves, and a removably attachable syringe or pump for inflating and deflating said balloons so as to provide adjustable compression over said arteries. The syringes or pumps referred to in this specification have a volume that can be filled with air or other gas, any portion of which, up to its capacity, may be injected into the balloons. Thus an operator may use the syringe or pump to inject varying amounts of air or gas into the balloons. Further, they are detachably connectable and re-usable so that they can further be used to withdraw or inject more air or gas during the course of a deployment onto a patient. Thus, these syringes or pumps have the characteristic of permitting an operator to make adjustments in the amount of air or gas present within the balloons.

It will be understood by those skilled in the art that, although the following drawings and Detailed Description disclose further aspects and advantages of the wristband and describes preferred embodiments, the present invention is not intended to be limited only to these preferred embodiments. It will be apparent that other changes in form and detail may be made therein without departing from the spirit and scope of the invention as defined in the appended claims.

BRIEF DESCRIPTION OF THE DRAWINGS

FIG. 1 is a bottom view of an adjustable radial and ulnar compression wristband.

FIG. 2 is a side section view of the wristband with parts removed for clarity.

FIG. 8 is a perspective end view, with parts removed for clarity, of a wristband with a movable inflatable cuff.

FIG. 9 is a perspective end view, with parts removed for clarity, of a wristband with two movable inflatable cuffs.

DETAILED DESCRIPTION OF THE PREFERRED EMBODIMENTS

Figure 3:
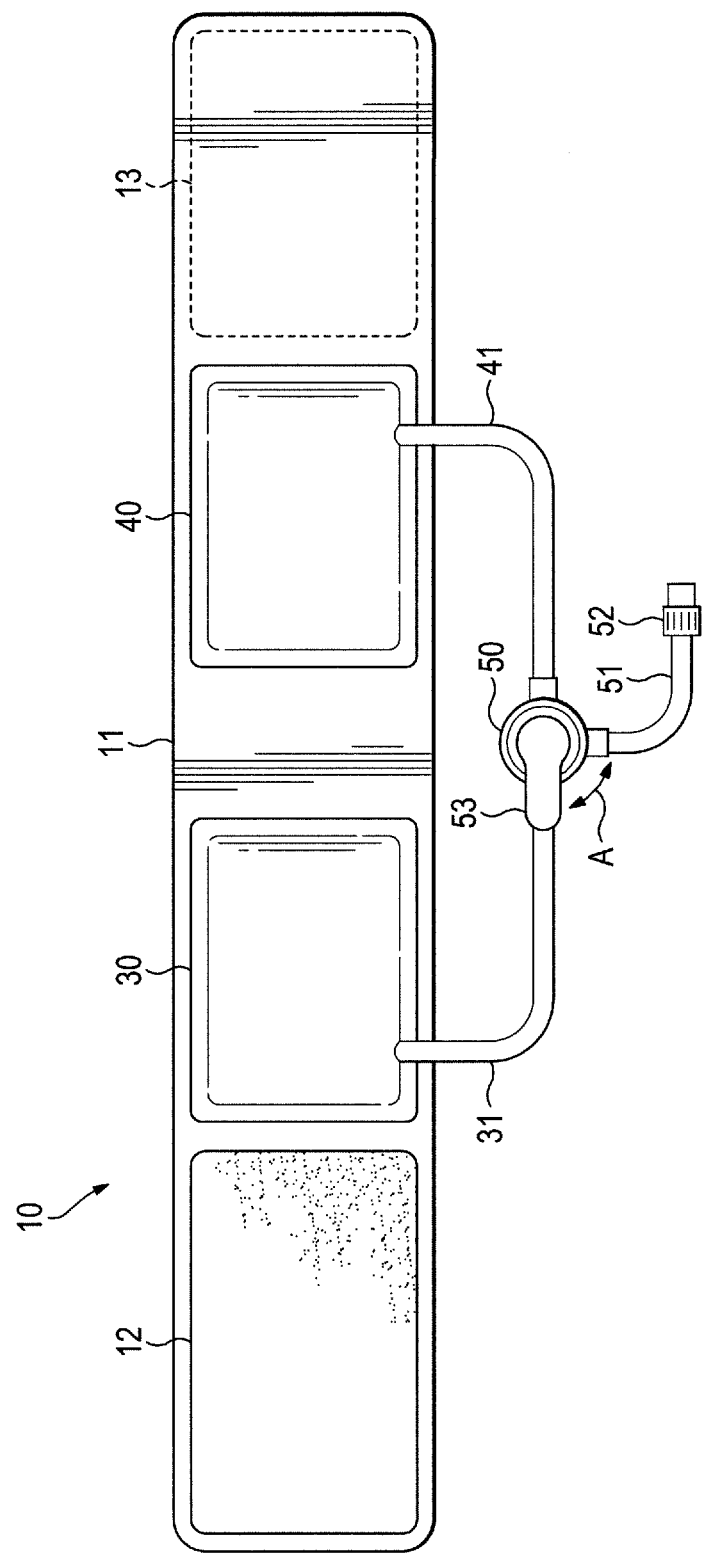
FIG. 3 is a bottom view of an alternative embodiment of the wristband.

An adjustable radial and ulnar compression wristband 10, for use in assisting with post-procedure radial artery hemostasis following catheterization or other cannulation, is shown in the Drawings and Detailed Description included herein as preferred embodiments of the present invention. Although parts are described as discrete components and features are described with specific structures, it will be understood by those skilled in the art that alternative means of construction to achieve the same purpose may be employed without deviating from the present invention.

The wristband 10 of the present invention generally includes at least: a flexible strap 11 having two ends; a securement means of fastening said strap circumferentially around a wrist or forearm preferably comprising "hook and loop" material, e.g. Velcro, the loop material 12 being placed at one end and the hook material 13 being placed at the opposite end of the strap 11; a compression means including at least two inflatable balloons, in a preferred embodiment comprising at least an ulnar balloon 30 and a radial balloon 40 separate from each other, to be positioned over the ulnar 103 and radial 101 arteries, and an inflation means and adjustment means for inflating and adjusting the interior volumes of said balloons 30 and 40. Said inflation means and adjustment means generally comprises hollow tubes 31 and 41, valve/connectors 32 and 42, and a syringe or pump operated by a user that can be attached to the valve/connectors 32 and 42. Each of the balloons 30 and 40 includes cavities 33 and 43 the injection of air or other gas into which causes inflation of the balloons 30 and 40. Injection of such air or other gas is made by means of the syringe or pump that attaches to the valve/connectors 32 and 42, such attachment being preferably removable, and the injection of air being adjustable by a user. Removable attachment is desirable so that patients are unable to make adjustments in the compression when the user removes the syringe or pump. The syringe or pump of the inflation means and adjustment means is further capable of adjustably withdrawing air or other gas from the cavities 33 and 43, thus the volumes contained therein may be adjusted by a user. In an alternative embodiment described herein, the compression means also includes a balloon 70, and may exclude other components as described in detail in this specification. Similarly, in such alternative embodiment, the inflation means and adjustment means also includes a cavity 73 of the balloon 70, tube 71 and valve/connector 72, in addition to the syringe or pump, and may exclude other components as described in detail in this specification.

In an alternative embodiment, the ulnar balloon 30 is absent from the strap 11, replaced by a cuff balloon 70, located on a slidably movable cuff 60 that slides along the strap 11 to enable greater flexibility in positioning compression over the ulnar artery 103, the cuff balloon 70 having a construction and inflation and adjustment means similar to the ulnar 30 and radial 40 balloons. This is shown in FIGS. 6A, 6B, 7A, 7B, 8 and 9. The balloons 30, 40 and 70 are non-adjacent, specifically not adjacent to each other, i.e. they do not rest one upon the other in the vertical axis and do not necessarily touch each other, except as may be the case when a user positions a cuff balloon 70 side by side next to the balloons 30 or 40. Further, it is within the scope of the invention that at least one of the balloons 30, 40, or 70 may be provided for use pre-inflated, i.e. air or gas has been injected such that no further inflation by the user is needed, thus an inflation means and adjustment means is not present on such balloon 30, 40 or 70.

FIGS. 1 and 2 shows the wristband 10 having a flexible strap 11, to which is attached a piece of loop material 12 at one end on the bottom side and a piece of hook material 13 at the opposite end on the top side; this hook 13 and loop 12 material together located on the strap 11 comprise a securement means for fastening the wristband 10 around a wrist 100. In the embodiment shown, the hook material 13 is positioned next to the radial balloon 40. On the bottom side of the strap 11 are formed or attached two inflatable balloons, comprising at least an ulnar balloon 30 and radial balloon 40., which extend substantially across the entire width of the strap 11 ans are non-movable relative to the ends of strap 11.Located between the balloons 30 and 40 and the strap 11 are, optionally, pieces of rigid backing, comprising the ulnar rigid backing 21 and radial rigid backing 22. During inflation of the balloons 30 and 40 the rigid backing pieces 21 and 22 provide a relatively rigid surface against which the balloons 30 and 40 press against, causing them to preferentially compress portions of the skin surface of a wrist 100. Attached to each of the balloons 30 and 40 are tubes, comprising at least the ulnar balloon tube 31 and radial balloon tube 41. To each of these tubes 31 and 41 are attached valve/connectors, comprising at least the ulnar balloon valve/connector 32 and radial balloon valve/connector 42. FIG. 2 further shows within each of the balloons 30 and 40 cavities 33 and 43. In this embodiment, the non-movcable balloons 30 and 40, tubes 31 and 41, connector/valves 32 and 42, together with a syringe or pump to inflate the cavities 33 and 43 of the balloons 30 and 40, comprise an inflation means and compression adjustment means for inflating the balloons 30 and 40, and adjusting compression applied over the radial 101 and ulnar 103 arteries.

The rigid backings 21 and 22 are separate from each other and in a preferred embodiment may be entirely absent from the wristband 10. Though the backings 21 and 22 would be absent, the space between the top surface of the balloons 30 and 40 and the underside of the strap 11 may optionally still be present to permit expansion of the balloons 30 and 40 such that the strap 11 provides the backing function. Additional layers of material may also be attached over the balloons 30 or 40 onto the strap 11 or thicker material may be used in order to provide a stronger, still-flexible backbone against which the balloons 30 or 40 may press against when inflated, to enable the same function as the rigid backings 21 and 22. Alternatively, multiple layers of material may be attached, one layer onto another, for the entire length and width of the strap 11, the layers being affixed to each other by means of adhesive, or by ultrasonic or radio-frequency welding or other means well-known to those skilled in the art, and additional layers being affixed along portions of the strap 11 to form features, for example, balloons 30 or 40. Further, this multiple-layer construction, i.e. the points of attachment of the layers, by forming a single layer from multiple layers, serves to strengthen the material so as to reduce the extent to which the material of the strap 11 can be stretched when the strap 11 is placed under load while in shear, more particularly when such points of attachment extend along the longitudinal axis or sections thereof, or when they extend across the entire width of the strap 11. Such points of attachment can further be used to form the balloons 30 and 40 from two or more layers of material. Such multiple-layer construction reduces stretching thus enabling the use of material for the strap 11 that is more compliant, thus more comfortable during deployment on a patient, compared to stiffer flexible material that, while stretching less in a single-layer construction, would be less comfortable particularly where the edges make contact with the patient's skin surface.

A line or other mark or marks may be placed in the center the radial balloon 40, running proximally-distally, as a visually observable guide to assist the user in proper placement of the radial balloon 40, i.e. generally over the radial artery 101. Such mark or line may alternatively be placed in the same position, but on the strap 11. Another line or other mark that perpendicularly crosses the first line or mark, the former positioned approximately ¼ to ½ of the proximal-distal length of the radial balloon 40 from its distal-most side may similarly be placed. The intersection of the two lines or marks further assists proper placement by indicating the general area of the radial balloon 40 that should be positioned over the puncture site 105.

FIG. 3 shows an alternative embodiment of the wristband 10 in which the tubes 31 and 41 are connected to a stopcock 50 connected to a tube 51 that is in turn connected to a valve/connector 52, to which is attached a syringe or pump used to inject air or other gas into the balloons 30 and 40, i.e. the inflation means. The stopcock 50, in this view, includes a switch stopcock lever 53. In this alternative embodiment the inflation means therefore further includes a switching means comprising the stopcock 50 and its switch stopcock lever 53 to switch airflow, through the tubes from the pump or syringe, from one balloon to the other, or to both simultaneously. Alternatively, the switching means may comprise a fixed, non-changeable connector that directs flow of air or gas to both balloons 30 and 40 simultaneously. The tubes 31 and 41 are connected at their opposite ends to the balloons 30 and 40 respectively, which are located on the strap 11. In this alternative embodiment, the balloons 30 and 40, tubes 31, 41 and 51, valve/connector 52, together with a syringe or pump to inflate the balloons 30 and 40, comprise a compression adjustment means, to adjust compression applied over the radial 101 and ulnar 103 arteries. Alternatively, the valve/connector 52 may be made integrally with the stopcock 50, avoiding the need to have a tube 51. The stopcock 50 together with switch stopcock lever 53, i.e. a switching means, is a means of directing air or gas flow to and from one or the other or both of the balloons 30 and 40 and different embodiments of such a switching means may be substituted without departing from the scope of the invention. The hook 13 and loop 12 material comprising a securement means are also shown.

Figure 4:
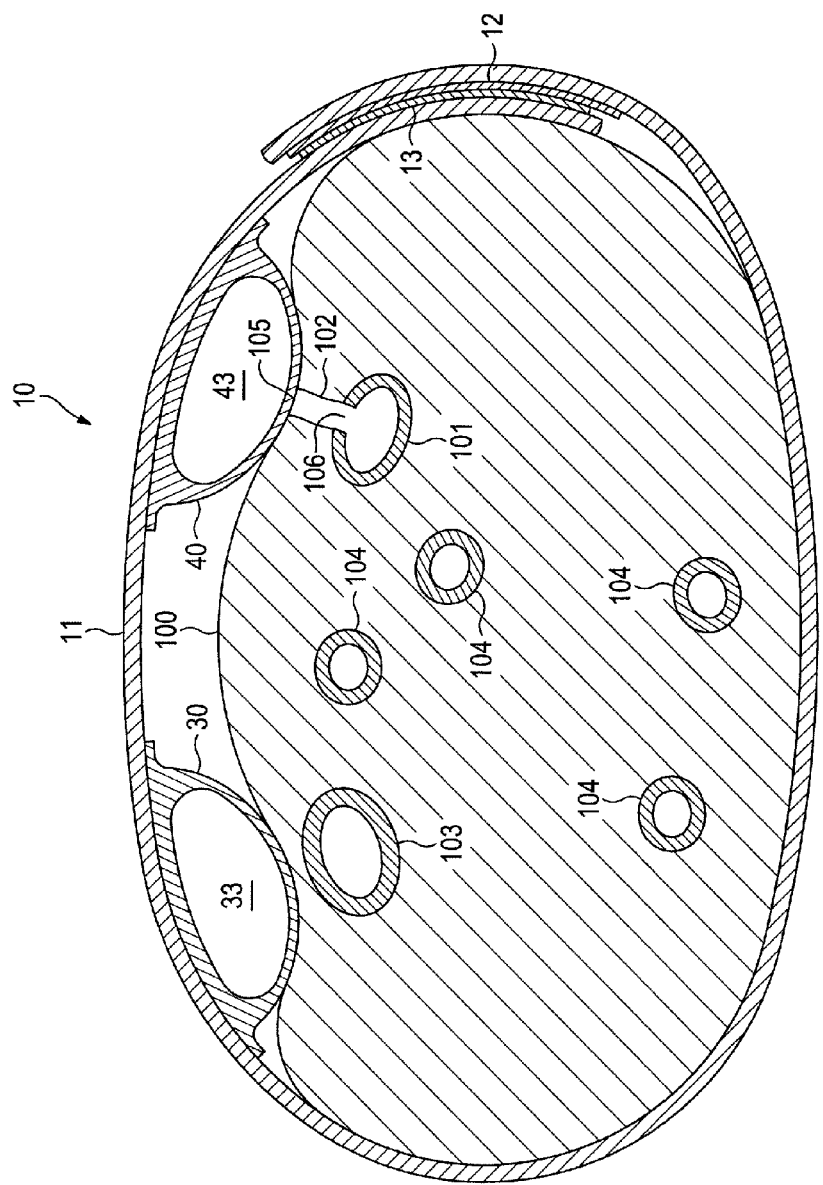
FIG. 4 is a section view, with parts removed for clarity, of the wristband deployed on a wrist.

FIG. 4 shows the wristband 10 deployed onto a wrist 100, the strap 11 having its two ends detachably fastened by means of the loop material 12 being attached to the hook material 13. This section view shows the balloons 30 and 40, non-movable attached to the strap 11, inflated with air or other gas injected and maintained inside the cavities 33 and 43, so as to apply compression onto portions of the surface of the wrist 100, such compression further being preferentially applied to the radial artery 101 and ulnar artery 103 located below the skin surface, such compression not being applied, at least to the same degree, to the veins 104 in the wrist 100. The radial balloon 40 is positioned over the access track 102, puncture site 105 and arteriotomy 106, through which the sheath passes into the radial artery 101. In this preferred embodiment, the rigid backing pieces 21 and 22 are absent and the strap 11, having thicker material or being formed as a multiple-layer construction, at least over the balloons 30 and 40, undertakes the backing function of these backing pieces 21 and 22 to preferentially compress portions of the skin surface underlying the balloons 30 and 40.

Figure 5:
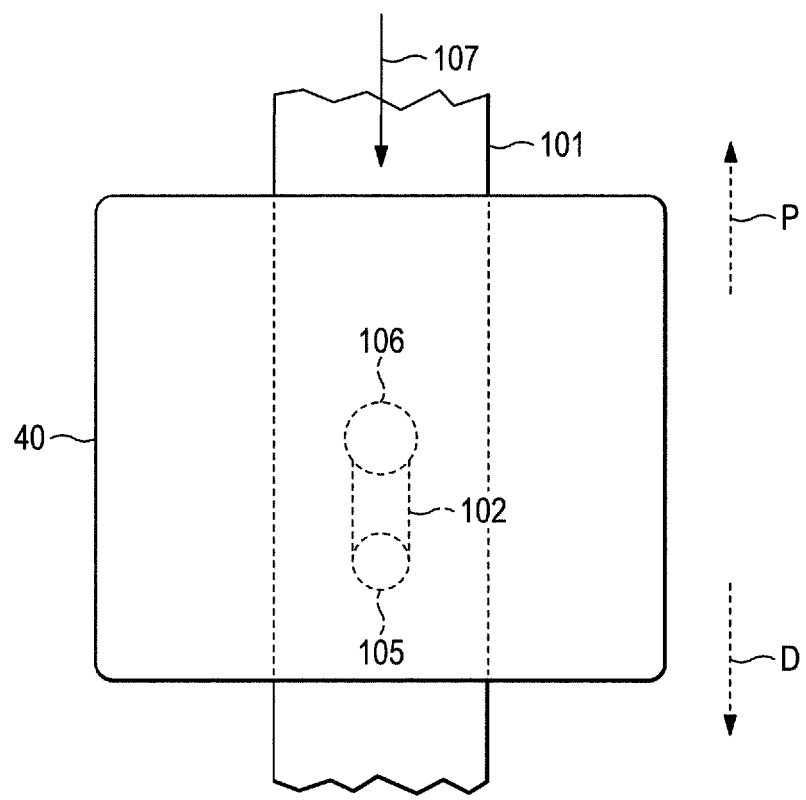
FIG. 5 is a top view, with parts removed for clarity, of the radial puncture site, with the wristband deployed on a wrist.

FIG. 5 shows, in top view with parts removed for clarity, the radial balloon 40 placed over the radial artery 101 and radial artery puncture site 105, with proximal P and distal D directions indicated. When inflated, the balloon 40 will provide compression over the puncture site 105, and the access track 102 that connects it to the arteriotomy 106 located proximally to the puncture site 105. The blood flow 107 passes proximally to distally past the arteriotomy 106, towards the hand. Size and placement of the radial balloon 40 provides sufficient surface area so that both the arteriotomy 106 and puncture site 105 are covered by the balloon 40. Lines or other marks placed on the radial balloon 40 as previously described in this specification assist in positioning over the radial artery 101 and puncture site 105.

Figure 6A:
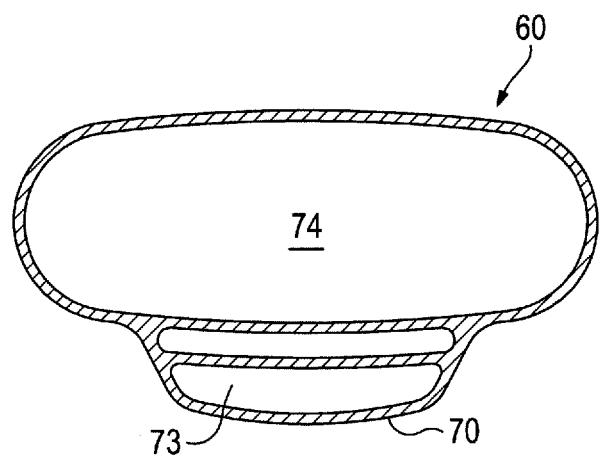
FIG. 6A is a section end view, with parts removed for clarity, of movable inflatable cuff.

FIG. 6A shows, in section end view with parts removed for clarity, a movable inflatable cuff 60 that includes a balloon 70 that further includes a cavity 73, and a lumen 74 through which the strap 11 passes. The cuff 60 may be slidably positioned along the strap 11 by a user. A space between the top surface of the balloon 70 and the underside of the cuff 60 is present to permit expansion of the balloon 70 such that the cuff 60 and strap 11 provides a backing function.

Figure 6B:
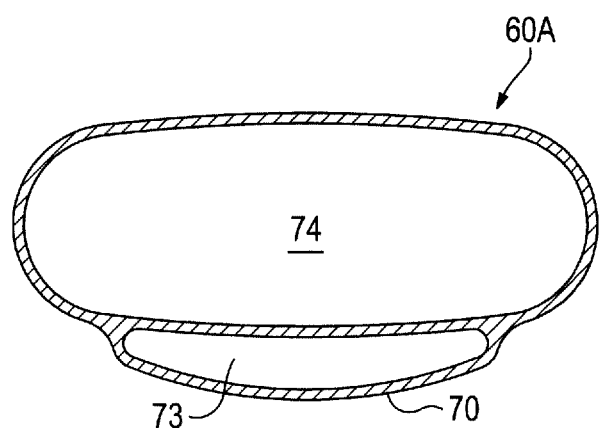
FIG. 6B is a section end view, with parts removed for clarity, of an alternative embodiment of a movable inflatable cuff.

FIG. 6B shows in section end view with parts removed for clarity an alternative embodiment of a movable inflatable cuff 60A that includes a balloon 70 that further includes a cavity 73, and a lumen 74 through which the strap 11 passes.

Figure 7A:
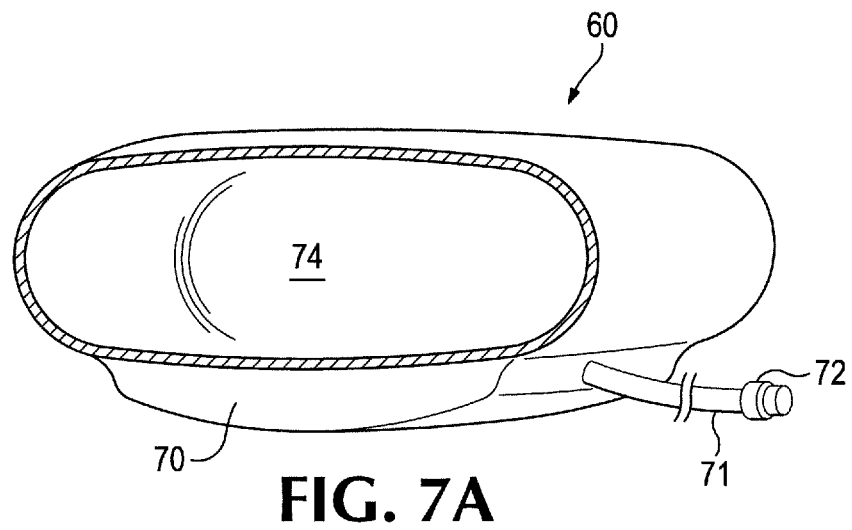
FIG. 7A is a perspective end view of a movable inflatable cuff.

FIG. 7A shows, in a perspective end view, a movable inflatable cuff 60 that includes a balloon 70 on its underside to which is connected a tube 71 and connector/valve 72. A lumen 74 permits slidable movement of a strap 11 therethrough. The balloon 70, tube 71, connector/valve 72, together with a syringe or pump to inflate the cavity 73 of the balloon 70, comprise an inflation means and compression adjustment means to inflate the balloon 70 and adjust compression applied over a blood vessel that more particularly may be the ulnar 103 or radial 101 artery. The syringe or pump would be connected to the connector/valve 72 for inflating and adjusting volume of air in the cavity 73.

Figure 7B:
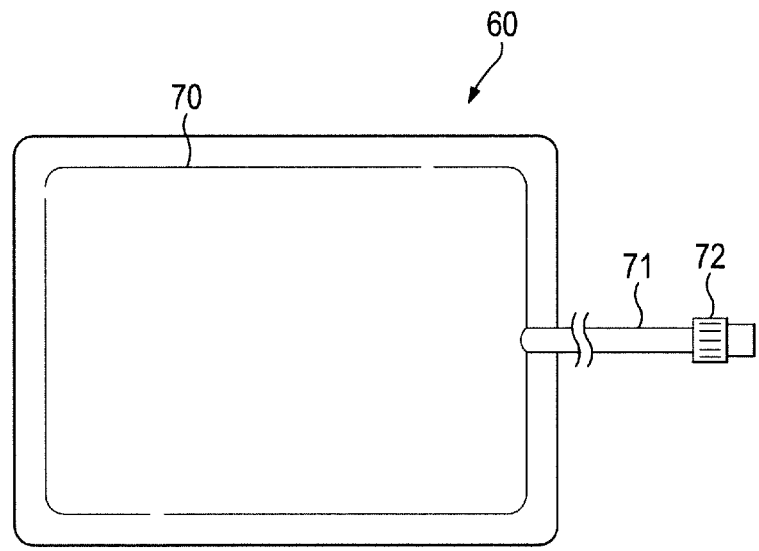
FIG. 7B is a bottom view of a movable inflatable cuff.

FIG. 7B shows, in a bottom view of a movable inflatable cuff 60, a balloon 70 to which is connected a tube 71 and connector/valve 72.

FIG. 8 shows, in a perspective end view with parts removed for clarity, an alternative embodiment of a wristband 10A with movable inflatable cuff 60, and strap 11A to which is attached loop material 12. The strap 11A, which lacks the ulnar balloon 30, passes through the lumen 74 of the cuff 60, so that slidable movement of each relative to the other is enabled. The cuff 60 further includes a balloon 70, shown on its underside, i.e. facing towards the skin surface. Attached to the balloon 70 are a tube 71 and connector/valve 72. Not shown on the strap 11A in this view is a radial balloon 40, tube 41 and valve/connector 42, and hook material 13. The cuff 60 is included with strap 11A, that has an attached non-movable radial balloon 40, the cuff 60 replacing the absent ulnar balloon 30, and is positioned by a user to compress the ulnar artery 103 during deployment onto a patient wrist 100.

FIG. 9 shows, in a perspective end view with parts removed for clarity, another embodiment of a wristband 10B with more than one inflatable cuff 60, each having a lumen 74, balloon 70, tube 71 and valve/connector 72, each of which can be slidably moved along the length of strap 11B. Absent from strap 11B are the ulnar 30 and radial 40 balloons. Also shown on strap 11B is the loop material. Included but not shown on strap 11B is the hook material 13, thus 11B includes a securement means. Other securement means besides hook 13 and loop 12 material may be used.

This embodiment thus includes two or more cuffs 60 with a strap 11B that lacks both the ulnar 30 and radial 40 balloons, the cuffs 60 being positioned by a user over the ulnar 103 and radial 101 arteries for compression at time of deployment. More than two cuffs 60 may be included with the strap 11, 11A or 11B, for positioning at various locations around a wrist 100 including over the ulnar 103 and radial 101 arteries, or to provide cushioning or elevate the interior surfaces of the strap 11A adjacent the balloon 70 off of the skin surfaces.

At time of deployment, the wristband 10 is placed around the wrist 100 with the balloons 30 and 40 facing towards the wrist and the radial balloon 40 generally over the radial artery 101 and puncture site 105. The wristband 10 is wrapped around the wrist 100 and fastened snugly by actuating the securement means, in this embodiment by attaching the loop material 12 to the hook material 13. The securement of the wristband 10 is thus maintained during the course of deployment, i.e. until hemostasis is achieved and the wristband 10 is removed. At the time of initial securement the balloons 30 and 40 are not inflated and a sheath is still present in the puncture site 105. A syringe or other pump is first connected to the valve/connectors 32 and 42, one at a time, and used to partially inflate the ulnar 30 and radial 40 balloons by injecting air or gas into the cavities 33 and 43. Such syringe or pump remains attached to the radial valve/connector 42 prior to pulling the sheath, still inside the puncture site 102. The sheath is then removed from the puncture site 102 and the syringe or pump is used to fully inflate the radial balloon 40 and then detached and attached to valve/connector 32 to further inflate the ulnar balloon 30. In the embodiment shown in FIG. 3, the syringe or other pump is connected to the valve/connector 52 and the switching means, i.e. the switch stopcock lever 53 as shown, is configured so as to direct the flows of air or gas into the cavities 33 and 43 of the ulnar 30 and radial 40 balloons, or to both balloons 30 and 40 simultaneously.

The inflated balloons 30 and 40 expand, changing their shape, due to the expanding volume of air or gas in the cavities 33 and 43. Because the wristband 10 is secured around the wrist 100, as the balloon 40 expands in the vertical direction, i.e. perpendicular to the plane of the surface of the wrist 100, it presses in the upward direction against the rigid backing 22 or in its absence against the strap 11, thus its expansion being contained in that direction, i.e. against a relatively fixed circumference of the strap 11. This causes the balloons' 30 and 40 expansion to proceed preferentially in the downward direction onto the more compliant soft tissue of the wrist 100. If the material or multiple-layer construction of the strap 11 provides sufficient strength to withstand excessive stretching or other deformation caused by the balloons' 30 and 40 expansion, with or without a backbone, the rigid backing 22 is not needed and excluded from the wristband 10, 10A or 10B. The balloons 30 and 40 therefore exert sustained compressive force onto the surface of the wrist 100 and the soft tissue structures directly underlying it, specifically the ulnar 103 and radial 101 arteries. Such compression flattens or narrows the lumen of the ulnar 103 and radial 101 arteries, such narrowing depending on the degree of compression exerted by the inflated balloons 30 and 40, and varying between completely closed or occluded, and open or patent. In none of the embodiments does one balloon apply compression or force onto another.

Though the shapes of the balloons 30, 40 and 60 are shown the drawings as rectangular, it is within the scope of the invention that they may also or instead have generally circular or oval shapes. Each balloon 30, 40, and 60 has a footprint sufficient to cover the area overlying its target blood vessel, either the radial 101 or ulnar 103 artery, and the puncture site 102, i.e. between 0.5 square inches and 3.0 square inches, more particularly between 1.5 and 2.5 square inches. The balloon over the radial artery 101 may be of different size than the balloon over the ulnar artery 103. When uninflated, the balloons 30, 40 and 60 are generally flat; when inflated, for example, with 20 cc of air or gas, they distend, gaining between 0.25 to 1.5 inches in the vertical dimension due to the stretch inherent in a flexible, elastic material from which the balloons 30, 40 and 60 are made. Such stretch is responsible for approximately a 10% to 50% decrease of compressive force during the first five minutes of inflation; thicker material or multiple-layer construction in the strap 11 or 11A results in a smaller decrease of compressive force. To accommodate wrists of varying size the length of the strap 11 is between 7.0 inches and 20.0 inches, more particularly between 8.0 and 14.0 inches, and the width between 0.75" and 2.25".

In an additional embodiment, a hemostatic agent, for example, generally composed of: i) chitosan or other polysaccharide such as a β-(1-4)-linked D-glucosamine (deacetylated unit) or N-acetyl-D-glucosamine, ii) thrombin, or iii) calcium alginate, or iv) compounds including minerals such as kaolin or potassium ferrate, is attached to the bottom of the balloons 30, 40, or 60, i.e. facing the skin surface, for the purpose of enhancing hemostasis of the puncture site 106 in conjunction with the compression provided by the inflated balloon 30, 40 or 60. Well known to clinicians involved with vascular access, these hemostatic agents are often applied as "patches" in conjunction with manual compression or with external compression devices. More particularly, a hemostatic agent, in the form of a solid material, is removably attached to the bottom surface of the balloons 30, 40 or 60 to permit it to remain on the puncture site 105 after the wristband 10 or 11 or 11A has been removed from the patient. Such removable attachment may take the form of an adhesive, or by placement on the bottom surface of a removable cuff encircling the balloon 30, 40 or 60 that can be held in place while the strap 10, 11 or 11A is unfastened and slidably moved therethrough for removal from the patient. If an adhesive is used, it may cover the entire top surface of the hemostatic agent patch for adhering to the bottom surface of a balloon 30, 40 or 60, or more preferably cover only a portion of such surface so that it i) may be more easily detached when the wristband 10 or 11 or 11A is removed, and ii) does not interfere with expansion of the balloons 30, 40 or 60 during inflation, adjustment and deflation. Any shape of hemostatic agent may be used, but preferably at least a portion of it protrudes past the edges of the balloons 30, 40 or 60 to more permit operator to hold it in place thus more easily enabling detachment when the wristband 10, 11 or 11A is removed from the patient. The size of the hemostatic agent can range from 5% of the bottom surface area of the uninflated balloons 30, 40 or 60 to 200% of such surface area.

Patent hemostasis, as described above in the background section, occurs when the lumen of the radial artery 101 is partially open thereby permitting a smaller than normal volume of blood flow 107 to pass therethrough while avoiding bleeding at the arteriotomy 106 and puncture site 105. Injecting more gas or air into the cavity 43 increases volume, thus further compressing the vessel lumen and further limiting the blood flow 107. Using the syringe or pump to withdraw gas or air from the cavity 43 decreases volume, thereby reducing compression of the lumen and increasing the volume of blood flow 107. Similar adjustments to ulnar balloon 30 compression enables varying degrees of patency in the ulnar artery 103.

The valve/connector 42 is closed when the syringe or pump is disconnected, thus generally preventing release of air or gas from inside the cavity 43. Alternatively, the valve/connector 42 may permit a pre-programmed volume of air or gas inside the cavity 43 to slowly leak out over a period of time. Following disconnection from valve/connector 42, the syringe or pump is then connected to the valve/connector 32 and is used to inflate the cavity 33 of the ulnar balloon 30 in a fashion similar to that already described for the radial balloon 40. Once both balloons 30 and 40 are inflated the syringe or pump may be re-attached to the valve/connectors 32 and 42 and the volume of air or gas increased or decreased in the cavities 33 or 43 so as to enable patent blood flow 107 through the radial artery 101 and ulnar artery 103 without concomitant oozing or bleeding at the puncture site 105. Patency can be readily determined using methods well known to clinicians, including direct manual palpation of the vessels, and use of doppler ultrasound, pulse oximeters or plethysmographs. The valve/connectors 32 and 42 may be check valves, swabable valves or other valves well known to those skilled in the art.

In the embodiment shown in FIG. 3, the syringe or other pump remains connected to the valve/connector 52 and the switching means is configured, following inflation of the balloon 40, so as to direct the flow of air or gas into the cavity 33 of the ulnar balloon 30. The ulnar balloon 30 is then inflated and the syringe or pump removed and re-inserted, if needed, as described above. Alternatively, the switching means may be set, either permanently or as desired by a user, so that inflation may be made simultaneously into both balloons 30 and 40. The switching means thus permits either user-controlled direction of air flow into the balloons, or a fixed, non-changeable air flow into the balloons. In all of the embodiments described herein, the flow of air or gas proceeds from a single balloon or all balloons to the syringe or pump, or vice versa, and not from one balloon to any other.

In the embodiment shown in FIG. 8, after inflating the radial balloon 40, the syringe or pump is disconnected from valve/connector 42 and then connected to the valve/connector 72 and used to inflate the cavity 73 of the cuff balloon 70 in a fashion similar to that already described for the ulnar balloon 30, the cuff 60 replacing the ulnar balloon 30. The cuff balloon 70 can be used to apply compression over the ulnar artery 103, or depending on an operator's preference over the radial artery 101, or over other portions of the wrist 100.

Although the embodiments presented herein show the valve and connector as the same physical component, i.e. as in the valve/connectors 32, 42, 52, and 72, the valve function may be physically separated from the connector function. It is within the scope of the invention that the valve function, i.e. the means of permitting air or gas flow into and out of and maintaining air within the cavities 33, 43, and 73 be a feature physically separate from the connector function, i.e. the means of removably attaching a syringe or pump. For example, the valve may be located at a point somewhere between the two ends of the tubes 31, 41, 51, or 71, or may be located at the point where the tubes 31, 41 or 71 joins the cavities 33, 43 or 73. An example of valve operation may comprise manual operation, valve closing achieved by the air pressure in the cavity 33 or 43 pressing on a movable obstruction within the valve housing against a seat, and valve opening achieved by increasing air pressure caused by operation of the syringe or pump pressing in the opposite direction on said movable obstruction away from the seat to permit air or gas flow. This may be combined with a spring to help maintain the obstruction in place against the seat when air pressure is low or nil. Alternatively, mechanical means may be used for controlling valve operation, for example a spring may be used to achieve valve closure and either a physical feature on the syringe or pump or air pressure exerted by the syringe or pump is used to achieve valve opening by pressing on a mating feature connected to the obstruction. Preferred embodiments are expected to have the valve and connector functions contained within the same component, for example a spring-operated or pressure-operated check valve or swabable valve, all of which are well-known to those skilled in the art.

The wristband 10 is not limited to having only two balloons 30 and 40 or 40 and 70 in its construction. Other balloons functioning similarly may be included at other locations on the strap 11 for the purpose of providing cushioning for the patient around the wrist 100, for example on the ulnar and radial sides of the wrist, and also to enable a standoff of the strap 11 from the surface of the wrist 100, more particularly on its dorsal side. In addition to previously presented embodiments, it is within the scope of the invention that the ulnar 30 and radial 40 balloons are present on the strap 11, and that a cuff balloon 70 also be included with the wristband 10 to provide an additional means for either compression or cushioning.

In the embodiments shown in the figures, the securement means is comprised of hook 13 and loop 12 material that, when joined together fastens the strap 11 around the wrist 100. It is within the scope of the invention that other mechanisms may comprise alternate securement means for the wristband 10, for example: a button and buttonholes, each being located at opposite ends of the strap 11; a belt slide or belt strip located at one end of the strap 11 through which the opposite end passes; a box frame buckle located at one end of the strap 11 through which the opposite end passes, an adjustable captive post sitting against the end of the strap 11 as it passes through the box frame to keep it in place by friction; a belt buckle located at one end of the strap having an open square frame and prong which passes through holes located at the other end of the strap 11; a plate style buckle located at one end of the strap 11 having a hook or pin that is inserted into holes at the other end of the strap 11. For purposes of describing these alternative securement means, the strap 11 in the foregoing paragraph also includes strap 11A and strap 11B.

Flexible, elastic transparent synthetic material, for example a vinyl, polyvinylchloride, polyethylene or polyurethane or nylon or similar material, may be used in the construction of the strap 11 and balloons 30 and 40. A more rigid transparent synthetic material, for example an acrylic or PVC or HDPE or PTFE or vinyl or nylon or polypropylene or polyethylene or similar material would be used in the construction of the optional rigid backings 21 and 22, in the event these are included on the straps 11, 11A or 11B. Preferably the materials are biocompatible and sterilizable. Further, the straps 11, 11A or 11B may be formed as a multiple-layer construction.

All or part of the wristband 10 may also be composed of a material having anti-microbial properties sufficient to prevent growth of microbes or to kill microbes with which it comes into contact, for example on the skin of a patient on whom the wristband 10 is deployed. Alternatively, the exterior surfaces of the wristband 10 or some of its components may be treated with a process or material having anti-microbial properties. Examples of these processes and materials, which are well-known to those skilled in the art, can include: i) the deposition of silver or organic or inorganic particles onto the surfaces of the components of the apparatus by means of vapor deposition or liquid immersion; or ii) including silver or organic or inorganic particles mixed into the materials from which the components are formed.

A method of using the wristband 10 includes the following steps:

i) Placement and securement of the wristband 10 onto the wrist 100. A user fits the wristband 10 around a wrist 100 of a patient and by attaching the loop 12 material to the hook 13 material fastens it snugly so that the uninflated radial balloon 40 is positioned over the radial artery 101 and puncture site 105, and the uninflated ulnar balloon 30 is positioned generally over the ulnar artery 103. Marks or lines placed on the radial balloon 40, strap 11 or backing 22 may assist in this positioning. When using an alternate embodiment of the wristband 10A as in FIG. 8, the user, prior to attaching the loop 12 to the hook 13 material, positions the cuff balloon 70 over the ulnar artery 103 by sliding the cuff 60 to the appropriate position; the user then fastens the loop 12 to the hook 13 material. When using an alternate embodiment of the wristband 10B as in FIG. 9, the user, prior to attaching the loop 12 to the hook 13 material, positions the cuff balloons 70 over the ulnar 103 and radial 101 arteries by sliding the cuffs 60 to the appropriate positions, i.e. over the target blood vessels; the user then fastens the loop 12 to the hook 13 material.

ii) Initial inflation of the balloons 30 and 40. A user attaches a syringe or pump to the valve/connector 32 and injects air into the cavity 33 to increase compression onto the skin surface of the wrist 100, thereby partially compressing the ulnar artery 103 such that the blood flow continues to pass therethrough but at a reduced flow rate. The user then attaches the syringe or pump to the valve/connector 42 and injects air into the cavity 43 via the tube 41 to inflate the balloon 40 to increase compression onto the skin surface of the wrist 100, thereby partially compressing the radial artery 101 such that the blood flow continues to pass therethrough but at a reduced flow rate. In the alternative embodiment of FIG. 3, the user attaches the syringe or pump to the valve/connector 52 instead of valve/connectors 32 and 42 and actuating the switching means to inject air into balloons 30 and 40. In the embodiment shown in FIG. 8, the user attaches the syringe to valve/connector 72 instead of valve/connector 32, then proceeds with inflation as described in the foregoing for balloon 30. In the embodiment shown in FIG. 9, the user attaches the syringe to valve/connectors 72 instead of valve/connector 32 and, then proceeds with inflation as described in the foregoing for balloons 30 and 40.

iii) Removing the sheath or cannula from the puncture site 105 and fully inflating the balloon 40. While preparing to further inflate the balloon 40 with the syringe or pump, the sheath or cannula is pulled from the puncture site 105. On complete removal of the sheath or cannula, the balloon 40 is fully inflated by injecting air with the syringe or pump into the cavity 43 through the valve/connector 42, such that there is no bleeding from the puncture site 105. In the embodiment shown in FIG. 9, the user attaches the syringe to valve/connector 72, to inflate cuff balloon 70, instead of valve/connector 42 and then proceeds with inflation as described in the foregoing for balloon 40.

iv) Adjusting inflation of the ulnar balloon 30. The user disconnects the syringe or pump from the valve/connector 42 and connects it to the valve/connector 32. In the alternative embodiment of FIG. 3, the user instead configures the switching means, e.g. the switch stopcock lever 53, to re-direct air into the ulnar balloon 30 and not the radial balloon 40. Air or gas is then injected into or withdrawn from the balloon 30 to adjust compression onto the skin surface of the wrist 100, to compress the ulnar artery 103 to slow or completely occlude blood flow therethrough. When using an alternate embodiment shown in FIG. 8 or 9, the user, instead of connecting the syringe to the valve/connector 32, connects it to the valve/connector 72 of the balloon 70 positioned over the ulnar artery 103 and inflates said balloon 70 to compress ulnar artery 103 as described in the foregoing for balloon 30.

v) Achieving patent hemostasis. The distal pulses of the radial 101 and ulnar 103 arteries are assessed using methods well-known to clinicians and include the Allen Test, Reverse Allen Test or Barbeau Test using palpation, pulse oximeters or plethysmographs, or ultrasound to detect pulses distal to the points of compression. In the event a distal pulse is not detected for the radial artery 101, the syringe or pump is used to gradually remove air or gas from the cavity 43 of the radial balloon 40 so as to reduce compression until a distal radial artery 101 pulse is detected without concomitant bleeding from the puncture site 105. Instead of or in addition to injecting into or withdrawing air or gas from the radial balloon 40, the syringe or pump may be used to gradually inject into or withdraw air from the ulnar balloon 30 or the cuff balloon 70 that is placed over the ulnar artery 103 until the distal radial artery 101 pulse is detected without concomitant bleeding from the puncture site 105. While the wristband 10 is deployed and applying compression, it may be gradually adjusted periodically by using the syringe or pump to inject into or withdraw air from the ulnar 30, radial 40 or cuff 70 balloons. In the embodiment shown in FIG. 9, the user attaches the syringe to valve/connector 72 of the cuff balloon 70 placed over the radial artery 101 instead of the valve/connector 42, and then proceeds with adjusting the inflation of said cuff balloon 70 as described in the foregoing for balloon 40.

vi) Removing the wristband 10 from the wrist 100. When hemostasis is achieved at the puncture site 105 and arteriotomy 102, for example after one or two hours of compression with patency present in both the ulnar 103 and radial 101 arteries, the syringe or pump is used to slowly withdraw air or gas from the balloons 30, 40 and 70 until the cavities 33, 43 and 73 are empty. The user may then separate the hook 13 material from the loop 12 material and remove the wristband 10 from the patient's wrist 100.

The present invention thus achieves its objectives through the embodiments and methods described herein. It will be understood that the present invention is not limited to the method or detail of construction, fabrication, material, application or use described and illustrated herein. Indeed, any suitable variation of fabrication, use, or application is contemplated as an alternative embodiment, and thus is within the spirit and scope of the invention. Accordingly, while the present invention has been shown and described with reference to the foregoing embodiments of the invented apparatus and method of use, it will be apparent to those skilled in the art that other changes in form and detail may be made therein without departing from the spirit and scope of the invention as defined in the claims.

It is further intended that any other embodiments of the present invention that result from any changes in application or method of use or operation, configuration, method of manufacture, shape, size, or material, which are not specified within the detailed written description or illustrations contained herein yet would be understood by one skilled in the art, are within the scope of the present invention.

We claim:

1. A means for achieving patent hemostasis of a puncture site in a blood vessel in a wrist that includes at least a flexible strap having a longitudinal length and two ends at opposite sides of the longitudinal length, a securement means for circumferential positioning and fastening the strap circumferentially around the wrist, and a compression means for applying preferential compression onto a radial artery and an ulnar artery in said wrist, said compression means including at least two inflatable non-adjacent balloons, a first balloon of said at least two inflatable non-adjacent balloons is for placement over the ulnar artery but not the radial artery of said wrist when a second balloon of said at least two inflatable non-adjacent balloons is over the radial artery but not the ulnar artery in said wrist, the second balloon of the balloons is non-movable relative to the two ends of said strap along the longitudinal length, and the first balloon is not non-movable and is located on a cuff slidably movable along the longitudinal length of the strap, and an inflation means and an adjustment means for adjustably applying said compression.

2. The inflation means and adjustment means of claim 1, further including a switching means for directing air or gas flow.

3. A wristband for the purpose of achieving patent hemostasis of a puncture site in an artery in a wrist, the wristband comprising at least: a flexible strap having a longitudinal length and a width and two ends at opposite sides of the longitudinal length, hook and loop material placed at the two ends of said strap, two inflatable non-adjacent balloons each having a top side positioned along a portion of the longitudinal length of the strap and a tube connecting each balloon to a connector, wherein:

each of the two balloons extends substantially across the entire width of the strap;

the two balloons are sized and positioned such that a first balloon of said balloons is for placement over an ulnar artery but not a radial artery of said wrist when a second balloon of said balloons is over the radial artery but not the ulnar artery in said wrist;

the second balloon of the balloons is non-movable relative to the two ends of said strap along the longitudinal length, and the first balloon is not non-movable and is located on a cuff slidably movable along the longitudinal length of the strap.

4. The wristband of claim 3 further including a syringe or pump that is removably attachable to the connector, wherein compression is adjustably applied preferentially by the balloons placed over the ulnar and radial arteries, by air or gas injected into or withdrawn from the balloons by operation of said syringe or pump.

5. At least one of the balloons of claim 3 is more particularly strengthened by including on its top side at least two layers of material, each affixed to the other along at least one portion of said top side.

6. The strap and balloons of claim 3, which are more particularly composed of one selected from the group of materials comprising polyvinyl chloride, vinyl, polyethylene, polyurethane or nylon material.

7. The wristband of claim 3, that further includes a hemostatic agent attached to a bottom surface of at least one of said balloons.

8. A wristband for the purpose of achieving patent hemostasis of a puncture site in an artery in a wrist, the wristband comprising at least: a flexible strap having a longitudinal length and a width and two ends at opposite sides of the longitudinal length, hook and loop material placed at the ends of said strap, two inflatable non-adjacent balloons each having a top side positioned along a portion of the longitudinal length of the strap, and a tube connecting each balloon to a connector, wherein:

each of the two balloons extends substantially across the entire width of the strap; the two balloons are sized and positioned such that a first balloon of said balloons is for placement over an ulnar artery but not a radial artery of said wrist when a second balloon of said balloons of said balloons is over the radial artery but not the ulnar artery in said wrist;

the second balloon of the balloons is non-movable relative to the two ends of said strap along the longitudinal length, and the first balloon is not non-movable and is located on a cuff slidably movable along the longitudinal length of the strap.

9. The wristband of claim 8 further including a syringe or pump that is removably attachable to the connector, wherein compression is adjustably applied preferentially by the balloons placed over the ulnar and radial arteries by air or gas injected into or withdrawn from the balloons by operation of said syringe or pump.

10. At least one of the balloons of claim 8 is more particularly strengthened by including on its top side at least two layers of material, each affixed to the other along at least one portion of said top side.

11. The wristband of claim 8, that further includes a hemostatic agent attached to a bottom surface of at least one of said balloons.

12. The strap and balloons of claim 8, which are more particularly composed of one selected from the group of materials comprising polyvinyl chloride, vinyl, polyethylene, polyurethane or nylon material.

\* \* \* \* \*